(12) United States Patent
Wu et al.

(10) Patent No.: US 8,759,096 B2
(45) Date of Patent: Jun. 24, 2014

(54) MICROFLUIDIC CHIP AND METHOD USING THE SAME

(75) Inventors: Chen-Wei Wu, Hsinchu (TW); Cheng-Hsien Liu, Hsinchu (TW); Chau-Ting Yeh, Hsinchu (TW); Hui-Ling Lin, Hsinchu (TW); Hsin-Yu Lai, Hsinchu (TW); Tzu-Chi Yu, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 1016 days.

(21) Appl. No.: 12/776,210

(22) Filed: May 7, 2010

(65) Prior Publication Data
US 2010/0216244 A1    Aug. 26, 2010

(30) Foreign Application Priority Data
Mar. 16, 2010   (TW) .............................. 99107681 A (51) Int. Cl.
*C12N 5/00* (2006.01)
*C12M 3/04* (2006.01)

(52) U.S. Cl.
USPC ...................... 435/373; 435/293.1; 435/294.1

(58) Field of Classification Search
CPC ....... C12M 23/16; C12M 35/00; C12M 35/04
USPC ................. 435/373, 288.5, 293.1, 294.1, 401
See application file for complete search history.

(56) References Cited

U.S. PATENT DOCUMENTS

| | | | | |
|---|---|---|---|---|
| 4,858,883 A | * | 8/1989 | Webster | 251/61.1 |
| 5,922,591 A | * | 7/1999 | Anderson et al. | 435/287.2 |
| 2002/0172969 A1 | * | 11/2002 | Burns et al. | 435/6 |
| 2010/0041128 A1 | * | 2/2010 | Banes et al. | 435/287.9 |
| 2012/0129207 A1 | * | 5/2012 | Yarmush et al. | 435/29 |

* cited by examiner

*Primary Examiner* — William H Beisner
(74) *Attorney, Agent, or Firm* — WPAT, P.C.; Anthony King; Kay Yang (57) ABSTRACT

Disclosed is a microfluidic chip and method using the same. The microfluidic chip comprises a substrate having a surface, and at least a tissue culture area formed on the surface of the substrate. The tissue culture area has a microfluidic channel formed by a plurality of connected geometrical structures (nozzle-type channels) having a predetermined depth. The microfluidic channel has an inlet and an outlet, which are at two ends of the microfluidic channel, for medium inputting and outputting, respectively. Additionally, at least an air-exchange hole is formed on the bottom of the microfluidic channel. By using the microfluidic chip for tissue culture, lateral flow speed and stress can be decreased, so as to prolong survival time of tissues (e.g. liver tissues).

7 Claims, 9 Drawing Sheets

MICROFLUIDIC CHIP AND METHOD USING THE SAME

This claims the benefit of priority under 35 U.S.C. Sec. 119 from the prior Taiwan Patent Application No. 099107681, filed Mar. 16, 2010, the entire content of which is hereby incorporated by reference in its entireties.

FIELD OF THE INVENTION

The present invention relates to a device for tissue culture, particularly relates to a microfluidic chip and a method using the same.

BACKGROUND OF THE INVENTION

Since human body systems are complicated, once researchers desire to realize how drugs influence a human body, they often firstly experiment at cellular level. According to the experiment results including a series of changes in cell morphology and metabolism, they may predict the probable model of human reaction, and evaluate activity and toxicity of the drugs. If experiments can be more directly implemented in tissue to identify their activity and toxicity, the results should be more close to human researches.

Traditional methods for culturing liver tissues include: (A) static culture, (B) dynamic culture, (C) single-sided perfusion culture, and (D) double-sided perfusion culture. The methods of (A) static culture and (B) dynamic culture both have a drawback that fresh medium can't efficiently diffuse into liver tissues. This causes that cells of liver tissues will die after static culturing for a while, and during the time they will lose their basic functions gradually then totally lose their functions in the end. Until now, the culturing period for a clinical liver tissue culture are 3 to 5 days at most. Although the methods of (C) single-sided perfusion culture and (D) double-sided perfusion culture may raise the viability of liver tissues by single-sided perfusion and double-sided perfusion. However, lacking of excellent designs of used apparatuses, the liver tissues cannot be efficiently supplied with nutrients yet. Without obtaining sufficient nutrients, the cells of liver tissues have a tendency to die, and it finally causes the whole liver tissue becomes necrotic. Therefore, it is advantageous to develop a device which may efficiently provide the liver tissues therein with sufficient nutrients, thus the viability can be raised.

As miniaturization technology becomes more and more mature, traditional culture dishes are gradually replaced by microchips. In particular, while performing researches for drugs, applying miniaturization technology can greatly save the amount of samples, and also perform multiple reactions simultaneously.

In order to combine advantages of the prior art and improve its drawbacks, as great efforts and plenty of experiments have done, the mcirofluidic chip of the present invention is finally developed. By the present invention, cultured tissues not only extend their survival time and maintain the basic functions but also accelerate the researches for drugs to human tissues through the miniaturization technology.

SUMMARY OF THE INVENTION

The objective of the present invention is to provide a microfluidic chip to efficiently culture tissues in vitro.

Another objective of the present invention is to provide a method for culturing tissues in vitro by utilizing the microfluidic chip as above.

In accordance with one aspect of the present invention, the microfluidic chip comprises: a substrate having a surface; at least a tissue culture area formed on the surface of the substrate, having a microfluidic channel formed by a plurality of connected geometrical structures having a predetermined depth, the microfluidic channel having an inlet and an outlet at two ends thereof for inputting the medium and outputting the same respectively, and at least an air-exchange hole being formed on the bottom of the microfluidic channel.

Preferably, the geometrical structures are nozzle-type channels.

Preferably, a predetermined angle is formed between the adjacent geometrical structures, so as to regulate the fluid field distribution of the medium.

Preferably, the predetermined angle between the adjacent geometrical structures has a range from 0 to 90 degrees.

Preferably, the predetermined angle of the adjacent geometrical structures preferably has a range from 45 to 90 degrees.

Preferably, the connected position between two of adjacent microfluidic channels has a predetermined width being capable of preventing the tissue from flowing with medium.

Preferably, the microfluidic channel is further attached with a polymer membrane.

Preferably, the polymer membrane is composed of polydimethylsiloxane (PDMS).

Preferably, a plurality of cells are cultured on the surface of polymer membrane.

Preferably, the cells are mesothelial cells.

Preferably, the substrate is composed of polymethylmethacrylate (PMMA).

Preferably, the tissue is an animal tissue.

Preferably, the tissue is an animal liver tissue.

Preferably, the microfluidic chip further comprises a top cover adapted to cover the substrate.

Preferably, the microfluidic preferably comprises a plurality of tissue culture areas, and the tissue culture areas are connected to form at least a one-dimensional array, wherein the array has an inlet and an outlet at two ends thereof.

Preferably, the substrate further has at least a side channel connected to the inlet of the array and the section between two connected tissue culture areas respectively.

In accordance with another aspect of the present invention, a method for culturing tissue in vitro utilizing the microfluidic chip as above is provided. The method comprises the steps of: (a) providing a polymer membrane being cultured with a plurality of cells thereon; (b) attaching the polymer membrane to the microfluidic channel of the microfluidic chip; (c) arranging a tissue on the polymer membrane; and (d) inputting a medium with a predetermined flow speed to the inlet of the microfluidic channel.

Preferably, the cells are mesothelial cells.

Preferably, the polymer membrane is composed of polydimethylsiloxane (PDMS).

Preferably, the tissue of step (c) is an animal tissue.

Preferably, the tissue of step (c) is an animal liver tissue.

Preferably, the medium of step (d) is inputted by an infusion pump.

Preferably, step (b) further comprises providing a mechanical force to suck the polymer membrane through the air-exchange hole, so that the deformed polymer membrane is attached to the microfluidic channel.

Preferably, the method further comprises a step of attaching a top cover to the substrate of the microfluidic chip after step (b).

BRIEF DESCRIPTION OF THE DRAWINGS

The above and other objects, features and other advantages of the present invention will be more clearly understood from the following detailed description taken in conjunction with the accompanying drawings in which.

DETAILED DESCRIPTION

Embodiment 1

Figure 1:
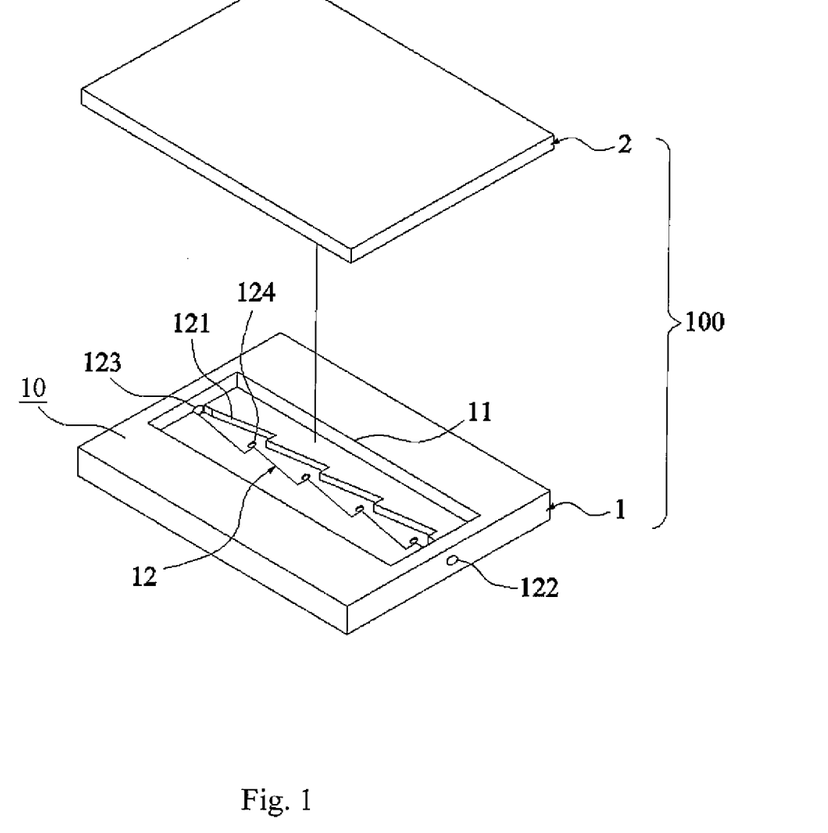
FIG. 1 is an exploded view showing the microfluidic chip according to the first embodiment of the present invention.
Figure 2:
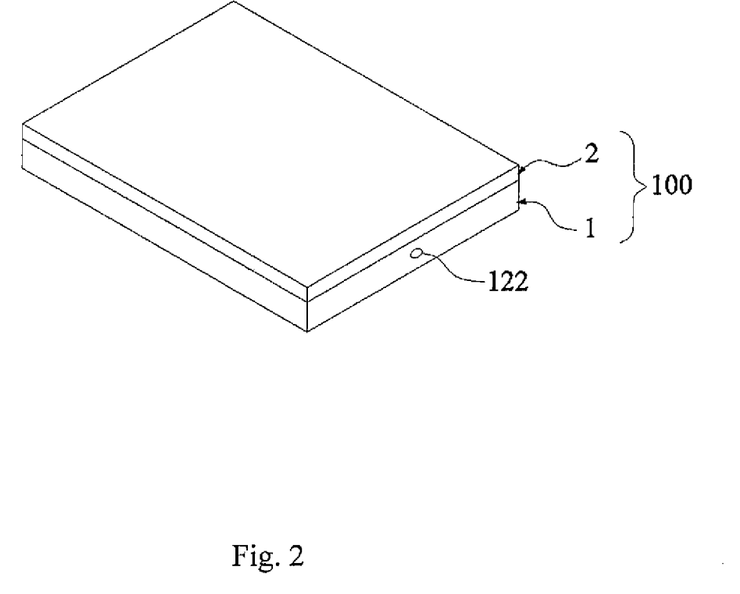
FIG. 2 is an assembly view corresponding to FIG. 1.

With reference to FIG. 1-FIG. 2, FIG. 1 is an exploded view showing the first embodiment of the present invention, and FIG. 2 is an assembly view corresponding to FIG. 1, In the first embodiment, microfluidic chip 100 is adapted to input and output a medium having a predetermined net flow speed so as to culture a tissue in vitro. As shown in figures, microfluidic chip 100 comprises a substrate 1 and a top cover 2. The substrate 1 is composed of polymethylmethacrylate (PMMA). The top cover 2 is adapted to cover the substrate 1.

The substrate 1 has a surface 10, and a tissue culture area 11 is formed on the surface 10 of the substrate 1 (It is exemplified in this embodiment by, but not limits to, only one tissue culture area). The tissue culture area 11 has a microfluidic channel 12 formed by a plurality of connected geometrical structures 121 having a predetermined depth. The microfluidic channel 12 has an inlet 122 and an outlet 123 at two ends thereof for inputting the medium and outputting the same respectively, and at least an air-exchange hole 124 being formed on the bottom of the microfluidic channel 12.

Figure 3:
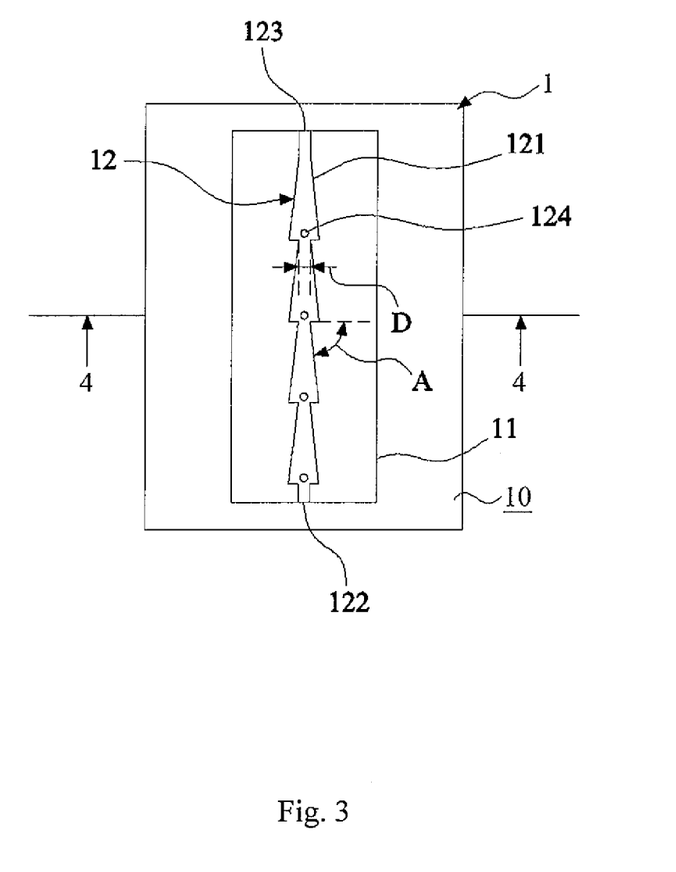
FIG. 3 is a top view showing the substrate of the first embodiment of the present invention.

With reference to FIG. 3, which is a top view showing the substrate of the first embodiment of the present invention. In this embodiment, geometrical structures are, but not limited to, nozzle-type channels, A predetermined angle A is formed between the adjacent geometrical structures 121. As shown in figure. 3, the angle A is defined between bottom of one geometrical structure and the slant of the next one. Due to the angle A, the fluid field distribution of the medium can be regulated with different angles. According to computer simulating results, the maximum flow speed is occurred in the position where one geometrical structure 121 connects to next one. Since the different angle results in the different flow speed, users may select a proper angle. The selected angle should depend on the position and bearable stress of cultured tissue in microfluidic chip 100, so as to resolve the problem that tissues can't be supplied with sufficient fresh medium. In order to lower lateral flow speed to decrease the effect for cells, the angle A is selected depending on actual required flow speed. Preferably, the angle A is from 0 to 90 degrees, so that cells can normally secrete proteins to supply for tissues. Particularly, it is desirable that the angle A is 84 degrees. The microfluidic channel 12 (connected position between two adjacent geometrical structure 121) has a predetermined width D capable of preventing the tissue from flowing with medium.

Figure 4:
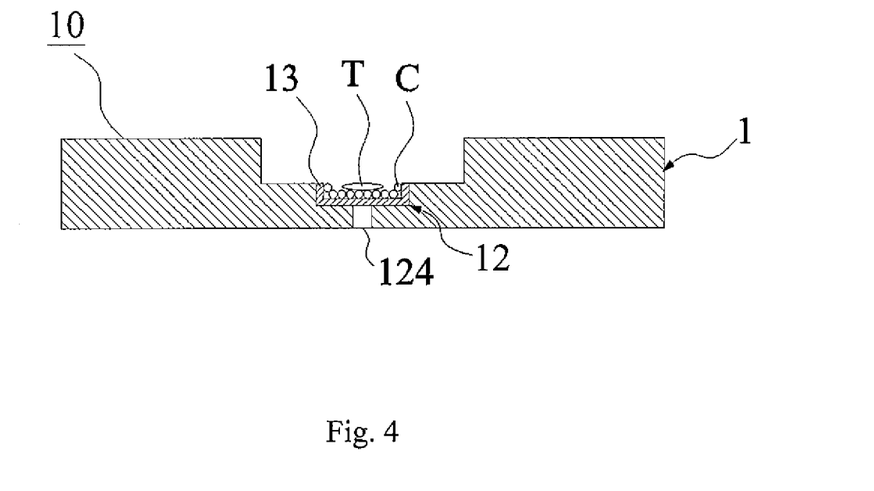
FIG. 4 is a sectional view showing the substrate with 4-4 cross-section.

With reference to FIG. 4, which is a sectional view showing the substrate with 4-4 cross-section. As shown in FIG. 4, the mierofluidic channel 12 is attached with a polymer membrane 13, which is composed of polydimethylsiloxane (PDMS) and flexible, and a plurality of cells C are cultured on the surface of polymer membrane 13. In this embodiment, the cells are mesothelial cells, and the cultured tissues T are animal liver tissues. The tissues are arranged on polymer membrane 13 and directly contact with the mesothelial cells. The animal liver tissues can obtain the required proteins secreted from mesothelial cells, so as to maintain their physiological functions, and to prolong their survival time.

Embodiment 2

Figure 5:
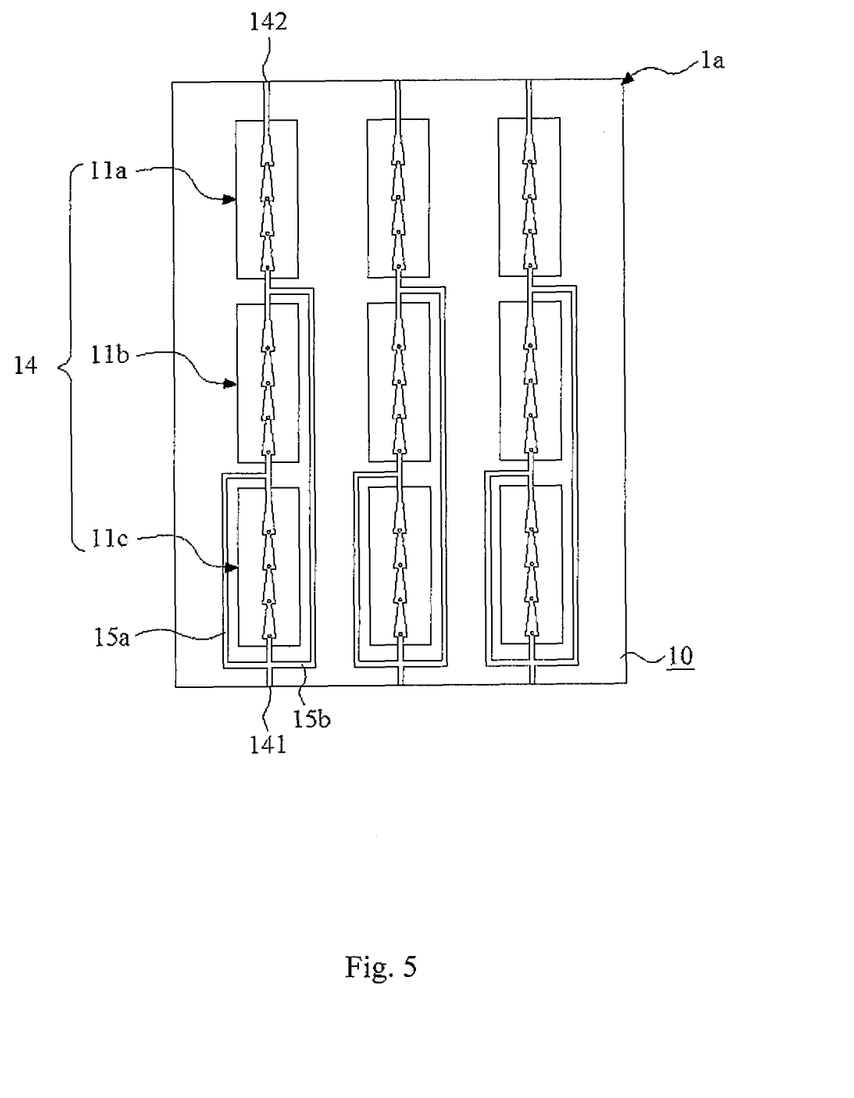
FIG. 5 is a top view showing the substrate of the second embodiment of the present invention.

With reference to FIG. 5, which is a top view showing the substrate of the second embodiment of the present invention. In this embodiment, the substrate 1a has three tissue culture areas 11a, 11b and 11c, serially connected to form a one-dimensional array 14. The array 14 has an inlet 141 and an outlet 142 at two ends and two side channels 15a, 15b formed thereon. One end of side channels 15a is connected to inlet 141 of array 14, and the other end is connected to the section between tissue culture areas 11b and 11c. Similarly, one end of side channels 15b is connected to inlet 141 of array 14, and the other end is connected to the section between tissue culture areas 11a and 11b.

Embodiment 3

Figure 6:
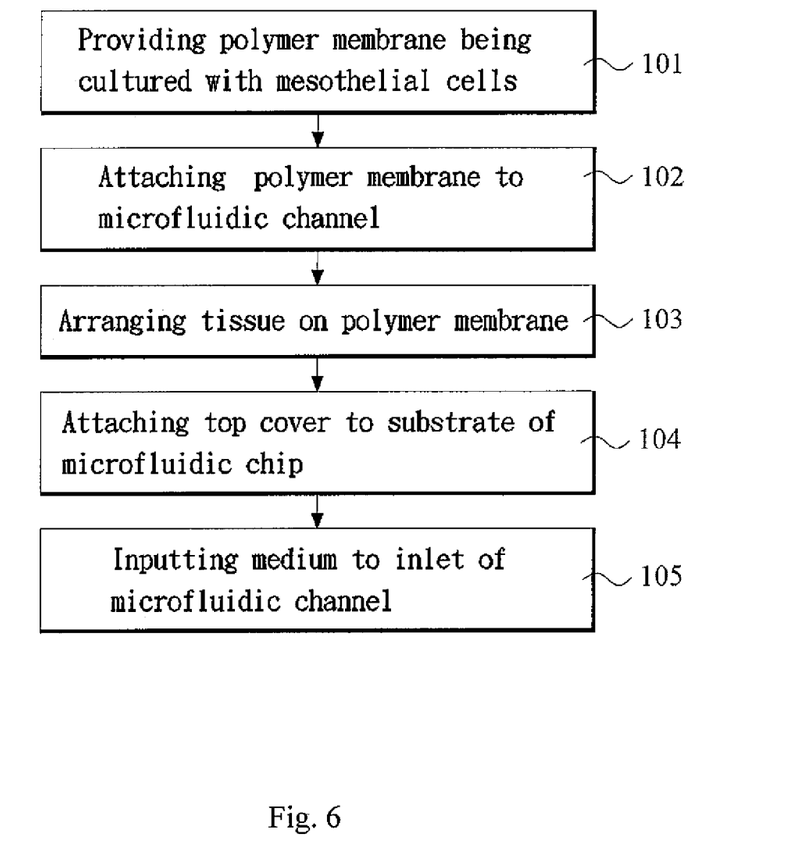
FIG. 6 is a flow chart of the third embodiment of the present invention.
Figure 7A:
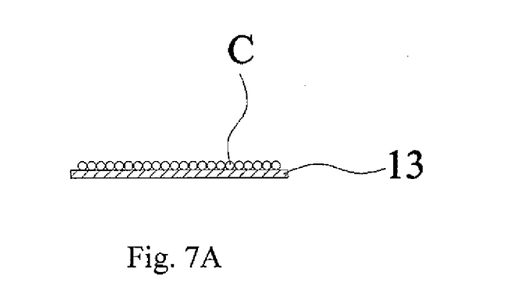
FIGS. 7A-7F are schematic views corresponding to the steps of FIG. 6.

With reference to FIG. 6 and FIGS. 7A-7F. FIG. 6 is a flow chart of the third embodiment of the present invention, and FIGS. 7A-7F are schematic views corresponding to the steps of FIG. 6. In this embodiment, a method for culturing tissue in vitro utilizing the foregoing microfluidic chip is provided. The method comprises the steps described as follow:

Step 101: Providing a polymer membrane 13 being cultured with a plurality of mesothelial cells C thereon. As shown in FIG. 7A, a plurality of mesothelial cells C are cultured on the polymer membrane 13 composed of PDMS. Clinical experiments indicate that mesothelial cells are capable of secreting some particular proteins which are helpful for culturing liver tissues. Based on this reason, mesothelial cells are cultured on the polymer membrane, so that the contact area between mesothelial cells and liver tissue can be increased, and the tissue may obtain more required proteins.

Figure 7B:
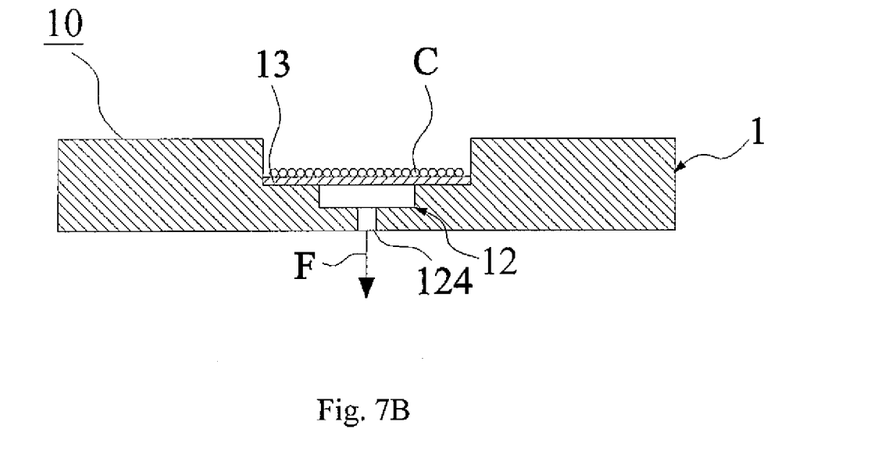
Figure 7C:
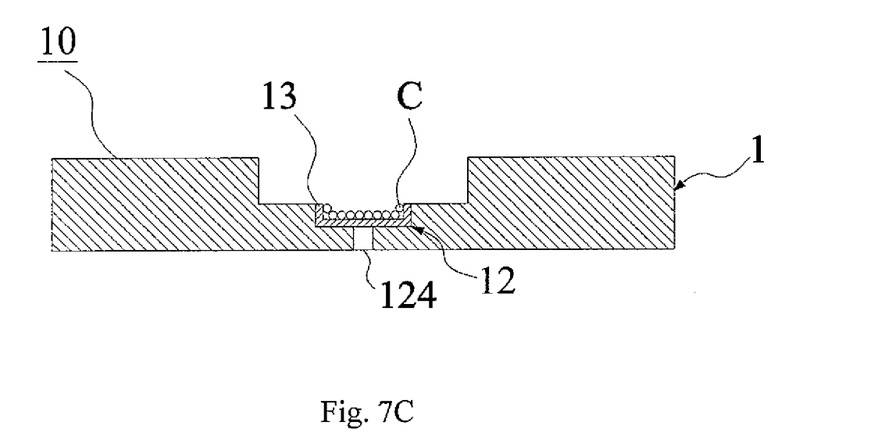

Step 102: Attaching the polymer membrane 13 to the microfluidic channel 12 of the microfluidic chip 100. As shown in FIGS. 7B and 7C, the polymer membrane 13 is placed over the microfluidic channel 12 of microfluidic chip 100. A mechanical force F is provided outside the air-exchange hole 124, and the polymer membrane 13 is sucked by mechanical force F through air-exchange hole 124. Due to polymer membrane 13 is composed of flexible material, it is forced to attached to the microfluidic channel 12.

Figure 7D:
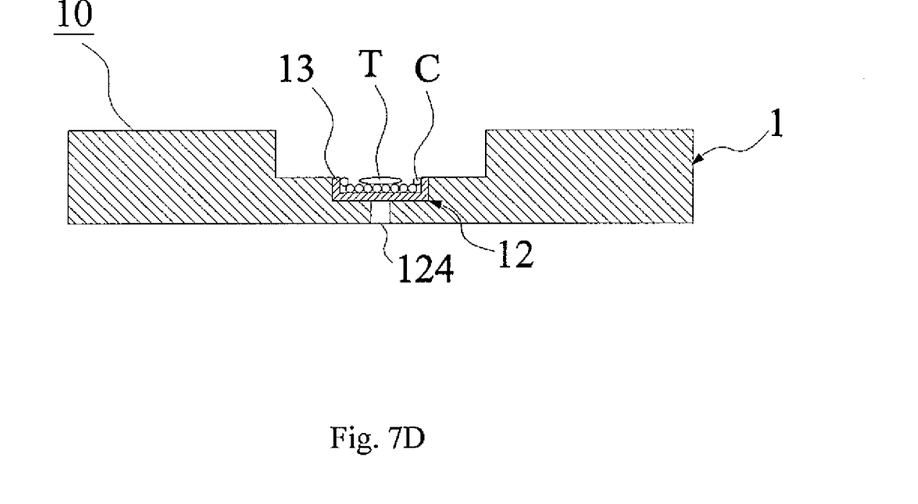

Step 103: Arranging a tissue T on the polymer membrane 13. As shown in FIG. 7D, the tissue T (e.g. animal liver tissue) is placed on the polymer membrane 13, and the tissue T can directly contact with the mesothelial cells C.

Figure 7E:
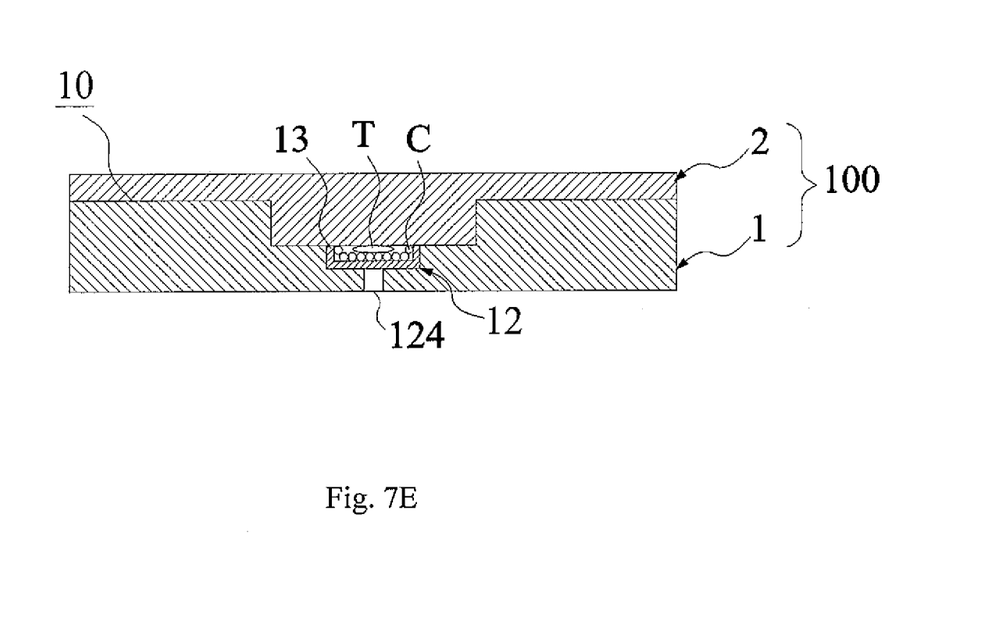

Step 104: Attaching a top cover 2 to the substrate 1 of the microfluidic chip 100. As shown in FIG. 7E, top cover 2 is tightly attached to the substrate 1.

Figure 7F:
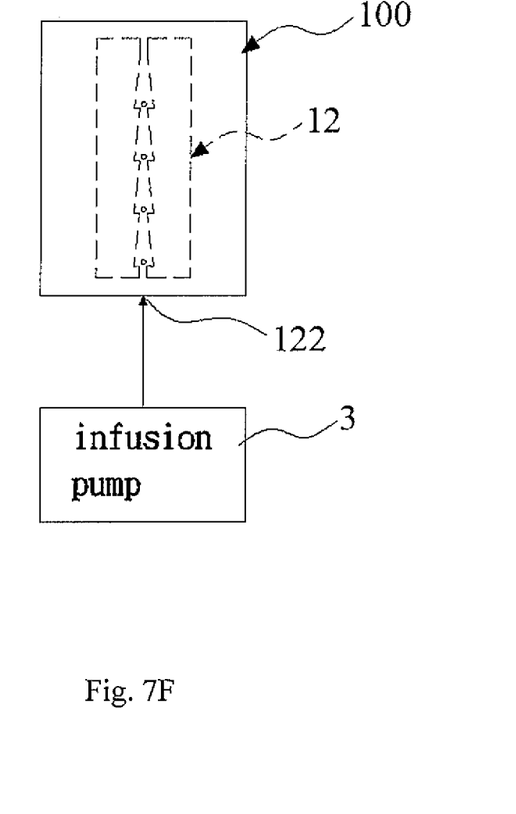

Step 105: Inputting a medium with a predetermined flow speed to the inlet 122 of the microfluidic channel 12. As shown in FIG. 7F, an infusion pump 3 is connected to the inlet 122 of microfluidic channel 12, and a medium with a predetermined flow speed is inputted into the microfluidic channel 12. The tissue T would be fixed in the connected position between two geometrical structures 121, so as to keep the tissue T from flowing with medium. Therefore, tissue T may secrete or receive the required proteins through the flowing medium.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A method for culturing tissue in vitro utilizing a microfluidic chip adapted to input and output a medium having a predetermined flow speed, comprising a substrate having a surface, and at least a tissue culture area formed on the surface of the substrate, having a single or a plurality of microfluidic channels formed by a plurality of connected geometrical structures having a predetermined depth, the microfluidic channel having an inlet and an outlet at two ends thereof for inputting the medium and outputting the same respectively, and at least an air-exchange hole being formed on the bottom of the microfluidic channel, wherein the method comprising the steps of:
   (a) providing a polymer membrane being cultured with a plurality of cells thereon;
   (b) providing a mechanical force to suck the polymer membrane through the air-exchange hole, so that the polymer membrane is attached to the single or the plurality of microfluidic channels of the microfluidic chip;
   (c) arranging a tissue on the polymer membrane; and
   (d) inputting a medium with a predetermined flow speed to the inlet of the microfluidic channel.

2. The method as claimed in claim 1, wherein the cells are mesothelial cells.

3. The method as claimed in claim 1, wherein the polymer membrane is composed of polydimethylsiloxane (PDMS).

4. The method as claimed in claim 1, wherein the tissue of step (c) is an animal tissue.

5. The method as claimed in claim 1, wherein the tissue of step (c) is an animal liver tissue.

6. The method as claimed in claim 1, wherein the medium of step (d) is inputted by an infusion pump.

7. The method as claimed in claim 1, further comprising a step of attaching a top cover to the substrate of the microfluidic chip after step (c).

* * * * *